United States Patent [19]

Mase et al.

[11] Patent Number: 4,505,790

[45] Date of Patent: * Mar. 19, 1985

[54] OXYGEN CONCENTRATION REGULATION

[75] Inventors: Syunzo Mase, Aichi; Shigeo Soejima, Nagoya, both of Japan

[73] Assignee: NGK Insulators, Ltd., Japan

[*] Notice: The portion of the term of this patent subsequent to Oct. 4, 2000 has been disclaimed.

[21] Appl. No.: 380,140

[22] Filed: May 20, 1982

[30] Foreign Application Priority Data

May 25, 1981 [JP] Japan .................................. 56-77921

[51] Int. Cl.$^3$ ............................................. G01N 27/46
[52] U.S. Cl. ..................................... 204/130; 204/425; 204/426; 204/427; 204/429; 219/553
[58] Field of Search ................. 204/1 S, 130, 421–429; 422/98; 219/505, 553

[56] References Cited

U.S. PATENT DOCUMENTS

| | | | |
|---|---|---|---|
| 3,400,054 | 9/1968 | Ruka et al. | 204/427 |
| 3,767,469 | 10/1973 | Flais et al. | 204/424 |
| 3,907,657 | 9/1975 | Heijne et al. | 204/427 |
| 4,145,272 | 3/1979 | Nakamura et al. | 204/412 |
| 4,321,577 | 3/1982 | Carlson | 422/98 |
| 4,427,525 | 1/1984 | Lin et al. | 204/412 |

FOREIGN PATENT DOCUMENTS

| | | | |
|---|---|---|---|
| 30164 | 6/1981 | European Pat. Off. | 204/427 |
| 0079246 | 6/1981 | Japan | 204/428 |

Primary Examiner—T. Tung
Attorney, Agent, or Firm—Parkhurst & Oliff

[57] ABSTRACT

An oxygen concentration regulator for regulating the oxygen concentration in gases comprises an oxygen ion conductive solid electrolyte body, at least two separate electrodes contacting the solid electrolyte body so as to form an electrolysis cell, said cell having complex impedance characteristics which when graphed exhibit a curve similar to that shown in FIG. 3 hereof, AC power supplying means for applying an AC electric voltage across said electrolysis cell, said AC power supplying means being operable only at an AC frequency which is not lower than a frequency whose complex impedance characteristics, when graphed in the manner shown in FIG. 3 hereof, correspond to point B of said graphed complex impedance characteristic curve, and means for affirmatively applying a DC current across said electrodes, said DC current regulating the oxygen concentration in gases.

The present invention is to provide an oxygen concentration regulator which can easily and efficiently control an oxygen partial pressure on at least one electrode side with a less power consumption and a simple structure.

19 Claims, 14 Drawing Figures

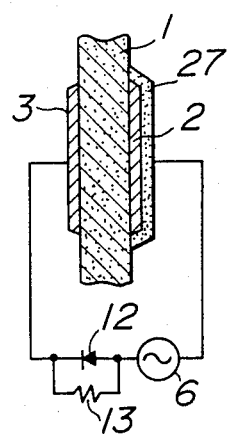
FIG._12
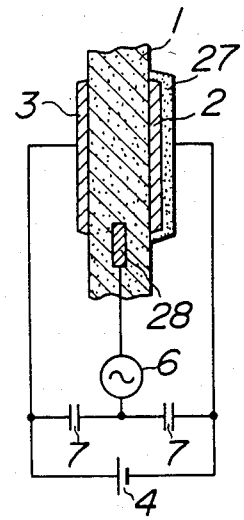
FIG._13
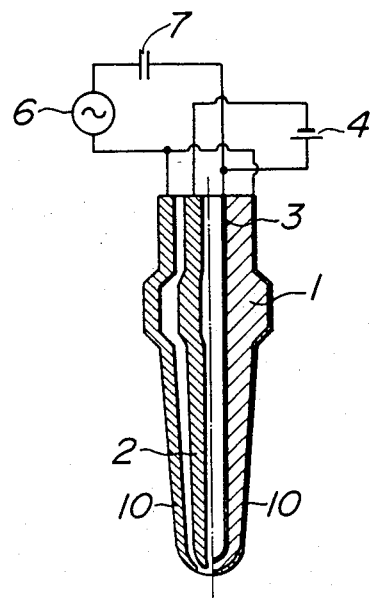
FIG._14

4,505,790

OXYGEN CONCENTRATION REGULATION

BACKGROUND OF THE INVENTION

1. Field of the Invention

The present invention relates to an oxygen concentration regulator using an oxygen ion conductive solid electrolyte.

2. Description of the Prior Art

As the oxygen concentration regulator of this type, there has hitherto been known an oxygen concentration regulator using, for example, a zirconia ceramics as the oxygen ion conductive solid electrolyte (hereinafter referred to as solid electrolyte), wherein the zirconia ceramics is used as a partition wall, a pair of electrodes such as platinum or the like are arranged on both sides of the partition wall, and a direct current voltage is applied across both the electrodes, whereby oxygen is moved from one of the electrodes to the other to control an oxygen concentration on one electrode side.

However, the solid electrolyte is small in electric conductivity at room temperature and becomes impractical, while higher temperature is required to reduce the polarization of the electrode such as platinum or the like, so that the above mentioned regulators are usually used in an electric furnace maintained at a high temperature. Therefore, the conventional oxygen concentration regulators with a system of flowing a direct current through the solid electrolyte have drawbacks that a large power is required for the heating of the electric furnace, and the structure of the regulator as a whole is complicated and becomes large-sized.

SUMMARY OF THE INVENTION

The present invention is to solve the above mentioned drawbacks of the prior art and provides an oxygen concentration regulator which can easily and efficiently control an oxygen partial pressure on at least one electrode side with a less power consumption and a simple structure.

The present invention relates to an oxygen concentration regulator for regulating the oxygen concentration in gases comprising an oxygen ion conductive solid electrolyte body; at least two separate electrodes contacting the solid electrolyte body so as to form an electrolysis cell, said cell having complex impedance characteristics which when graphed exhibit a curve similar to that shown in FIG. 3 hereof; AC power supplying means for applying an AC electric voltage across said electrolysis cell, said AC power supplying means being operable only at an AC frequency which is not lower than a frequency whose complex impedance characteristics, which when graphed in the manner shown in FIG. 3 hereof, correspond to point B of said graphed complex impedance characteristic curve; and means for affirmatively applying a DC current across said electrodes, said DC current regulating the oxygen concentration in gases.

An object of the present invention is to provide an oxygen concentration regulator, wherein at least one of said electrode is embedded in said electrolyte body.

Another object of the present invention is to provide an oxygen concentration regulator, which further comprises a refractory material which covers at least one of said electrode.

Further object of the present invention is to provide an oxygen concentration regulator, which further comprises means for limiting DC current level through the cell, means for preventing DC current from flowing into the AC power supplying means.

Still further object of the present invention is to provide an oxygen concentration regulator, which further comprises means for separating a circuit connected to AC power supplying means from the terminal of said electrolysis cell.

Another object of the present invention is to provide an oxygen concentration regulator, wherein said AC power supplying means comprises an AC power source and at least one AC electrode separated from said electrodes forming said electrolysis cell.

Another object of the present invention is to provide an oxygen concentration regulator, wherein at least a part of said means for flowing a DC current is a rectifying means for rectifying a part of said AC current into a DC current component.

Another object of the present invention is to provide an oxygen concentration regulator for regulating the oxygen concentration in gases, comprising:

an oxygen ion conductive solid electrolyte body;

a first set of at least two separate electrodes contacting the solid electrolyte body so as to form an electrolysis cell;

at least a third electrode separated from the electrodes of said first set; and

AC power supplying means connected to said third electrode for applying an AC electric voltage through said solid electrolyte body; and means for flowing a DC current across said first set of electrodes, said DC current regulating the oxygen concentration in gases.

Another object of the present invention is to provide an oxygen concentration regulator, wherein the solid electrolyte body has a tubular shape closed at one end and one of the two separate electrodes is on the inside of the tube and closed end, and the other of the two separate electrodes is on the outside of the tube and closed end.

Another object of the present invention is to provide an oxygen concentration regulator, further comprising means for limiting DC current level through the cell, and means for preventing DC current from flowing the AC power supplying means.

Another object of the present invention is to provide an oxygen concentration regulator, wherein at least one of said electrode is embedded in said electrolyte body.

Another object of the present invention is to an oxygen concentration regulator, further comprising a refractory material which covers at least one of said electrode.

Another object of the present invention is to an oxygen concentration regulator, wherein an alternating current and an alternating voltage between the electrodes have a negative relation, in which when one increases, the other decreases.

Another object of the present invention is to an oxygen concentration regulating cell comprising:

an oxygen ion conductive solid electrolyte body of tubular shape having one closed end having one of two separate cell electrodes contacting the inner surface of the tube and closed end, and the other of said two separate cell electrodes contacting the outer surface of said tube and closed end, and a third electrode separate from each of said two cell electrodes, said third electrode also contacting the outer surface of said tube.

Another object of the present invention is to a method of regulating oxygen concentration in a gaseous environment using an electrolysis cell comprising the steps of:

providing at least one electrolysis cell having at least two separate electrodes contacting an oxygen ion conductive solid electrolyte body, at least one of said electrodes being exposed to gas in a gaseous environment;

heating the solid electrolyte body by applying an AC voltage across at least two separate electrodes, and thereby decreasing the impedance of said cell; and flowing the DC current across the electrodes which comprises the electrolysis cell when said solid electrolyte body is in its heated condition, said DC current regulating the oxygen concentration around at least one of said electrode.

Another object of the present invention is to a method of regulating oxygen concentration in a gaseous environment using an electrolysis cell, wherein at least a part of said DC current are supplied by rectifying a part of AC component.

Another object of the present invention is to a method of regulating oxygen concentration in a gaseous environment using an electrolysis cell comprising the steps of:

providing at least one electrolysis cell having at least two separate electrodes contacting an oxygen ion conductive solid electrolyte body, at least one of said electrodes being exposed to gas in a gaseous environment; and said cell having a complex impedance characteristic curve similar in shape to that of FIG. 3 hereof;

applying an AC voltage across at least two separate electrodes with a frequency such that the cell is operated only at an AC frequency which is not lower than a frequency which corresponds to its complex impedance characteristics, which when graphed in the manner shown in FIG. 3 hereof correspond to point B of said graphed complex impedance characteristic curve; and flowing the DC current across the electrodes which comprise the electrolysis cell when said solid electrolyte body is in its heated condition, said DC current regulating the oxygen concentration around at least one of said electrode.

Another object of the present invention is to a method of regulating oxygen concentration in a gaseous environment using an electrolysis cell, wherein the solid electrolyte body is heated to at least about 350° C. by application of the AC voltage across said electrodes.

Another object of the present invention is to a method of regulating oxygen concentration in a gaseous environment using an electrolysis cell, wherein the solid electrolyte body has a tubular shape closed at one end and one of the two separate electrodes is on the inside of the tube and closed end, and the other of the two separate electrodes is on the outside of the tube and closed end.

Another object of the present invention is to a method of regulating oxygen concentration in a gaseous environment using an electrolysis cell, wherein said applied frequency is such that the complex impedance characteristics when graphed in the manner of FIG. 3 hereof corresponds to point C of said graphed complex impedance characteristics.

BRIEF DESCRIPTION OF THE DRAWINGS

The present invention will now be described in detail with reference to the accompanying drawings, wherein:

FIG. 12 is a diagrammatic view of another embodiment illustrating a refractory material which covers at least one of said electrodes;

FIG. 13 is a diagrammatic view of another embodiment illustrating an electrode embedded in an electrolyte body; and FIG. 14 is a diagrammatic view of another embodiment illustrating third electrode provided in electrolyte body.

DESCRIPTION OF THE PREFERRED EMBODIMENT

Figure 1:
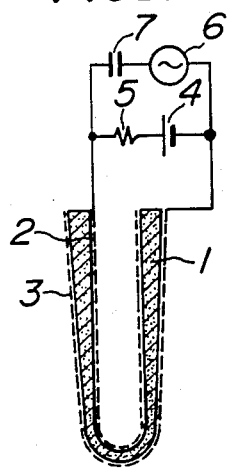
FIG. 1 is a diagrammatic view of an embodiment of the oxygen concentration regulator according to the present invention.

Referring to FIG. 1, a pair of inner and outer platinum electrodes 2, 3 are arranged on inner and outer sides of a bottomed cylindrical solid electrolyte 1 made of zirconia ceramics, and an alternating voltage is applied from an alternating current supply source 6 through a current limiting capacitor 7 to the electrodes 2, 3 at such a frequency that a polarization of an alternating current component occurs mainly due to a polarization of the solid electrolyte 1, whereby the solid electrolyte 1 is self-heated at a temperature of about 300° C. to 1,000° C. capable of giving a practical oxygen ion conductivity. Then, a direct current is applied from a direct current supply source 4 through a current limiting resistor 5 to the electrodes 2, 3, whereby oxygen ion is moved from the electrode 3 as a cathode to the electrode 2 as an anode to control an oxygen partial pressure on each side of the electrode such that the oxygen partial pressure on the side of the electrode 2 is higher than that on the side of the electrode 3. Moreover, when the arrangement of cathode and anode is opposite to the above case, the oxygen partial pressure on the side of the electrode 3 may be higher than that on the side of the electrode 2. In any case, the solid electrolyte 1 is directly self-heated by the application of alternating voltage, so that the heating of the solid electrolyte can be performed with a very low power consumption.

According to the present invention, the reason why the solid electrolyte can be heated by the application of alternating voltage without adversely affecting on the solid electrolyte and electrodes is based on the following fact.

Figure 2:
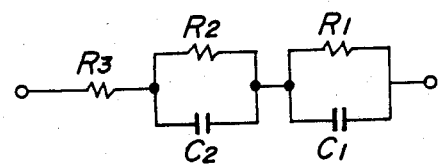
FIG. 2 is an equivalent circuit diagram of the oxygen concentration regulating cell.
Figure 3:
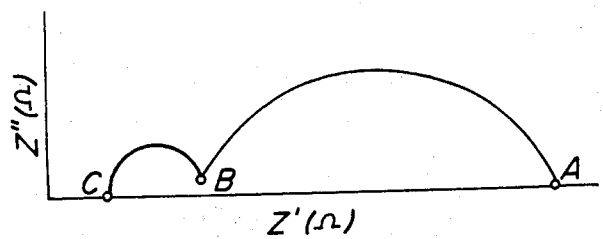
FIG. 3 is a graph showing complex impedance characteristics of the oxygen concentration regulating cell.

Namely, the oxygen concentration regulator provided with electrodes arranged on both sides of the solid electrolyte has an impedance equivalent circuit as shown in FIG. 2, wherein $R_1$ is a resistance at an interface between electrode and solid electrolyte, $C_1$ is an electrostatic capacitance resulted from a polarization of the interface between electrode and solid electrolyte, $R_2$ is a resistance at the crystal grain boundaries of the solid electrolyte, $C_2$ is an electrostatic capacitance at the crystal grain boundaries of the solid electrolyte, and $R_3$ is a resistance in the crystal grain of the solid electrolyte. In the oxygen concentration regulator having such an equivalent circuit, the frequency characteristic of the impedance takes a locus of two continuous arcuates as shown in FIG. 3 according to an indication of complex impedance $Z=Z'-jZ''$, in which a value of point A corresponds to the sum of $R_1+R_2+R_3$ in FIG. 2, a value of point B corresponds to the sum of $R_2+R_3$, and a value of point C corresponds to the value of $R_3$. Moreover, the polarization of the oxygen concentration regulator from the point A to the point B is mainly due to $R_1$ and $C_1$, while the polarization from the point B to the point C is mainly due to $R_2$, $R_3$ and $C_2$. With respect to the relation of the points A, B and C to the frequency, the impedance at the point A is obtained for direct current, and as the frequency increases, the complex impedance varies along the arcuate locus toward the point B and further along the other arcuate locus toward the point C.

The impedance of the oxygen concentration regulator varies in accordance with the temperature of the solid electrolyte and as the temperature becomes higher, the values at the points A, B and C become smaller and the frequencies at the points B and C become higher.

According to the present invention, when the self heating of the solid electrolyte is performed by applying an alternating current having a frequency not lower than the point B, i.e. an alternating current having a frequency at which a polarization of the alternating current component occurs mainly due to a polarization of the solid electrolyte, the applied alternating current has a value enough to heat the solid electrolyte, which causes no peeling-off of the electrode nor deterioration of the solid electrolyte. That is, when applying the alternating current having a frequency higher than that of the point B, the greater part of the polarization is produced inside the solid electrolyte due to $R_2$, $C_2$ and $R_3$, but is uniformly dispersed toward the thickness direction of solid electrolyte, so that the deterioration of the solid electrolyte hardly occurs during the application of the above alternating current. On the other hand, the polarization hardly occurs in the interface between the electrode and the solid electrolyte corresponding to $R_1$ and $C_1$ usually causing the deterioration, so that the application of the alternating current does not exert on the above interface. Moreover, the impedance at the region from the point B to the point C is determined by the properties inherent to the solid electrolyte and is hardly affected by the adhered state of the electrode, the change in long use time or the like, so that such an impedance is a stable value considerably lower than the direct current resistance. Therefore, when applying the alternating voltage at the frequency not lower than the point B, the solid electrolyte can stably be self-heated at a relatively low value of the applied voltage. In general, the value of resistance $R_1$ becomes rapidly higher as compared with resistances $R_2$ and $R_3$ as the temperature lowers, so that there is restricted the lower limit of the operating temperature of the oxygen concentration regulator. According to the present invention, however, the alternating voltage having a frequency at which the polarization of alternating current component occurs mainly due to the polarization of the solid electrolyte, i.e. the alternating voltage having the frequency not lower than the point B is applied to the oxygen concentration regulator as a means for reducing the influence of $R_1$, whereby the solid electrolyte is self-heated at the value of $R_2+R_3$ or the value of $R_3$ resulted from the polarization of the solid electrolyte independently of the value of $R_1$. Thus the AC power supplying means is so arranged as to supply an AC voltage at a frequency sufficiently high that the impedance between electrodes to which AC voltage is applied is largely independent of the interface capacitances between these electrodes and the surface of the electrolysis cell.

Even when the polarization of the alternating current component occurs mainly due to the polarization of the solid electrolyte, it is preferable to perform the self heating at such a frequency that the impedance of $C_2$ in FIG. 2 is smaller than the resistance $R_2$ in order to prevent the local heating of the solid electrolyte.

Figure 4:
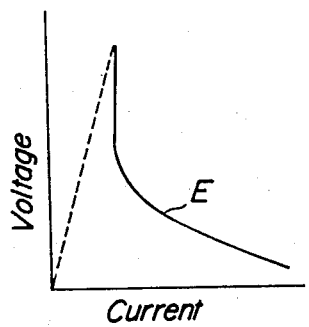
FIG. 4 is a graph showing current voltage characteristics when an alternating current voltage is applied to the solid electrolyte.

The relation between the alternating current and the alternating voltage applied to the solid electrolyte is shown in FIG. 4, from which it is apparent that when the alternating current is more than a determined value, the alternating current exhibits a negative relation to the alternating voltage (a curve E). This phenomenon is due to the fact that when the solid electrolyte is heated by the application of alternating current, the solid electrolyte itself acts as a temperature control means as mentioned later in FIG. 6. Therefore, in case of heating the solid electrolyte, it is preferable to apply the alternating current at a region of the curve E showing the negative relation, whereby the applied alternating voltage can be lowered in accordance with the self heating temperature.

Figure 5:
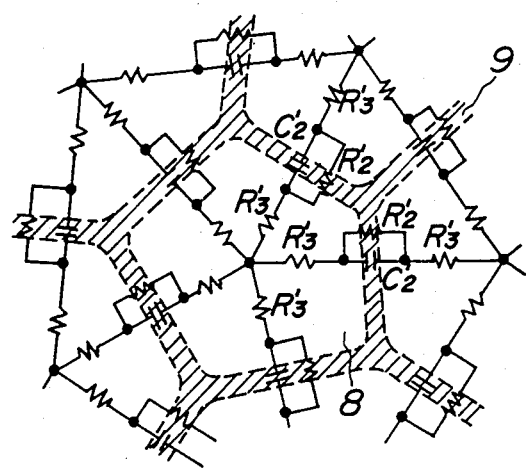
FIG. 5 is a partial diagrammatic view showing a relation between the microstructure of the solid electrolyte and the equivalent circuit.

Furthermore, each value of $R_2$, $C_2$ and $R_3$ inside the solid electrolyte is not single resistance or capacitance but is a sum of resistances $R'_2$, $R'_3$ or capacitances $C'_2$ of individual microcrystal grains 8 and high-resistance regions 9 existent between the grains 8, which constitute the solid electrolyte and are uniformly dispersed therein, as diagrammatically shown in FIG. 5. According to the present invention, even when the temperature of one grain 8 is raised by some reason to lower the resistance $R'_3$, electric current $i'$ does not flow over a value of $i'=2\pi fC'_2v'$ predetermined by capacitance $C'_2$ connected to the particular resistance $R'_3$, applied voltage $v'$ and frequency f. In this case, the values of the applied voltage $v'$ and capacitance $C'_2$ in one of the high-resistance regions 9 are very small, so that the electric current flowing through the region 9 becomes smaller and hence the local concentration of electric current is prevented. As a result, there is caused no local heating as seen in the case of merely flowing direct current through the solid electrolyte in the conventional oxygen concentration regulator or the case of applying alternating current within a low frequency range from the point A to the point B, so that even when the electrodes are arranged on both sides of a plate-shaped solid electrolyte, the whole of this solid electrolyte can uniformly be heated.

Moreover, the frequency from the point B to the point C depends upon the composition, temperature and shape of the solid electrolyte, the shape of the electrode and the like and is not constant. In the oxygen concentration regulator as shown in FIG. 1, when a pair of platinum electrodes are arranged on inner and outer wall surfaces of a bottomed cylindrical ceramics produced by adding 3 parts of clay to 100 parts of a mixture of 95 mol% of $ZrO_2$ and 5 mol% of $Y_2O_3$ and having an outer diameter at its closed end of 3.5 mm, an effective length of 10 mm and a thickness of 0.75 mm, the frequency at 350° C. is 10 Hz at the point B and more than about 50 KHz at the point C.

As the solid electrolyte to be used in the oxygen concentration regulator according to the present invention, mention may be made of zirconia ceramics, thoria ceramics, ceria ceramics and the like each containing yttrium oxide, ytterbium oxide, calcium oxide, magnesium oxide or the like as a stabilizing agent and further preferably containing aluminum oxide, silicon oxide, boron oxide or the like.

As the electrode, use may be made of any electric conductors resistant to a predetermined temperature, an example of which includes metals such as nickel, silver, gold, platinum, rhodium, palladium, ruthenium and the like; zinc oxide, $LaCoO_3$ and the like. The arrangement of the electrode on the solid electrolyte can be carried out by any usually used methods of adhering electrode to ceramics or the like, such as vacuum evaporation, sputtering, electroless plating, thermal decomposition or reduction of metal salt solution, baking of metal powder paste, cermet, spraying and the like. In order to prevent the evaporation or contamination of the electrode in use, the electrode may be protected with a refractory layer or embedded in the solid electrolyte.

Then, the application method of alternating current and direct current will be described with respect to the oxygen concentration regulator according to the present invention. As shown in FIG. 1, for instance, an alternating current supply source 6 is connected to electrodes 2, 3 arranged on a solid electrolyte 1 through a current limiting capacitor 7 and then an alternating current required for the heating of the solid electrolyte is applied across the electrodes 2, 3 from the alternating current supply source 6. In this case, the presence of the current limiting capacitor 7 can prevent the flowing of excessive current through the solid electrolyte 1, and also electric power applied to the solid electrolyte 1 is suppressed small at a high temperature region requiring no heating. The current limiting capacitor 7 may be a resistor or an inductor.

Figure 6:
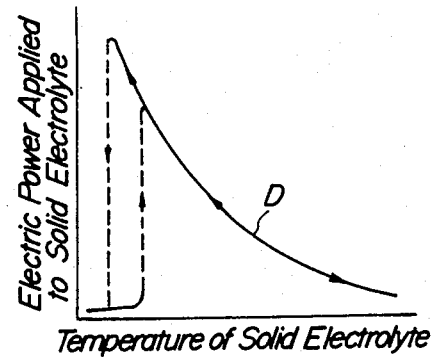
FIG. 6 is a graphical representation showing a self-temperature controlling property of the oxygen concentration regulator according to the present invention.

The relation between the temperature of the solid electrolyte 1 and the electric power applied thereto is shown in FIG. 6, from which it is apparent that when this relation is existent in a negative characteristic region as shown by a curve D in FIG. 6, the solid electrolyte itself develops the temperature control function.

Figure 7:
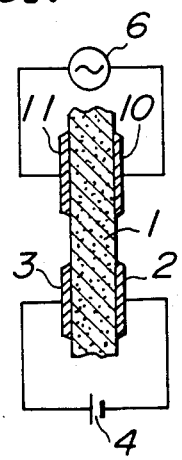
FIGS. 7 to 9 are diagrammatic views of embodiments illustrating a connected state between electrode and supply source in the oxygen concentration regulator according to the present invention, respectively.
Figure 8:
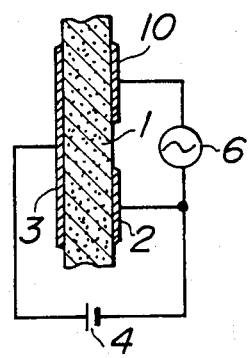

As shown in FIG. 1, the electrodes 2, 3 may serve for both the alternating and direct currents. Furthermore, as shown in FIG. 7, electrodes 10, 11 for the alternating current may be arranged independently of the electrodes 2, 3 for the direct current. Moreover, as shown in FIG. 8, either of the electrodes 2, 3 for the direct current may serve as an electrode for the alternating current.

Figure 9:
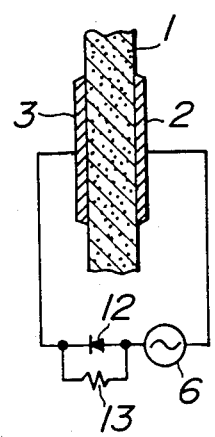

Next, a direct current supply source 4 is connected to the electrodes 2, 3 through a current limiting resistor 5 as shown in FIG. 1 and thereafter a direct current required for the control of an oxygen concentration is applied across the electrodes 2, 3 from the direct current supply source 4. In order to control the oxygen concentration, it is preferable to make any one of the supply source 4 and the resistor 5 variable. Alternatively, as shown in FIG. 9, the application of direct current may be performed by rectifying a part of the alternating current applied for the heating through a diode 12 and a resistor 13.

The solid electrolyte used in the present invention may take any shapes of plate, cylinder, bottomed cylinder, thin film and the like. In order to facilitate the flowing of electric current, a portion of the solid electrolyte to be self-heated is made thinner than the other remaining portion or kept warm, whereby this portion can stably be heated at a highest temperature as compared with the other remaining portion. Moreover, since the solid electrolyte to be heated has a large resistance at a low temperature owing to the negative resistance temperature characteristic, there is a case that electric current cannot be sufficiently applied during the heating. In such a case, an auxiliary heater is embedded in the solid electrolyte or arranged in the vicinity of the solid electrolyte, whereby the solid electrolyte may be preheated to a temperature capable of sufficiently flowing the electric current.

The following examples are given an illustration of the present invention and are not intended as limitations thereof.

EXAMPLE 1

Figure 10:
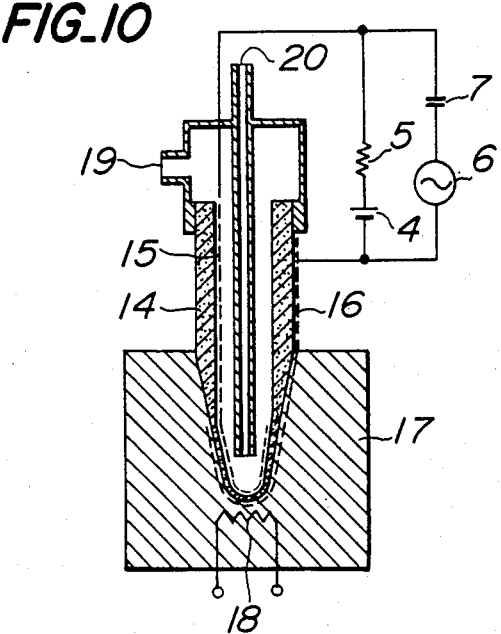
FIGS. 10 and 11 are diagrammatic views of other embodiments of the oxygen concentration regulator according to the present invention, respectively.

In an oxygen concentration regulator as shown in FIG. 10, a pair of platinum electrodes 15, 16 were arranged on inner and outer wall surfaces of a bottomed cylindrical zirconia ceramics 14 having a composition of 97 mol% of $ZrO_2$ and 3 mol% of $Y_2O_3$ and being mainly a tetragonal phase. The bottomed portion of the zirconia ceramics 14 was covered with a heat insulating layer 17 composed of alumina fibers and a preheater 18 was arranged near the above bottomed portion in the heat insulating layer. At first, electric current was applied to the preheater 18 to heat the bottomed portion of the zirconia ceramics 14 up to 300° C. Immediately after the application of electric current to the preheater was stopped, an alternating current was applied at 100 V, 0.5 A and 200 KHz from an alternating current supply source 6 through a current limiting capacitor 7 across the electrodes 15, 16. After 30 seconds of the application of alternating current, the temperature of the bottomed portion of the zirconia ceramics 14 was raised to 800° C., but the temperature change was not observed afterwards. Then, a direct current of 15 mA was applied from a direct current supply source 4 through a current limiting resistor 5 across the electrode 15 as an anode and the electrode 16 as a cathode, during which a nitrogen gas was fed from an inlet port 19 to the inside of the zirconia ceramics 14 at a rate of 500 ml/min. As a result, the nitrogen gas containing an oxygen concentration of 100 ppm was discharged from an outlet port 20. In this case, a terminal voltage of a direct current component applied across the electrodes 15, 16 was 1.1 V.

Moreover, when the value of the direct current to be applied was changed by using a variable resistance as the resistor 5, the oxygen concentration in the discharged nitrogen gas was completely proportional to the changed value of direct current. In this case, the frequencies at points B and C of FIG. 3 in the zirconia ceramics were 10 Hz and 10 KHz at 300° C., and 10 KHz and 10 MHz at 800° C., respectively.

EXAMPLE 2

Figure 11:
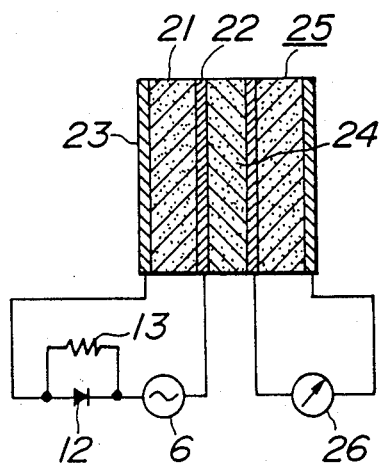

In an oxygen concentration regulator as shown in FIG. 11, a pair of platinum electrodes 22, 23 were arranged on both sides of a plate-shaped zirconia ceramics 21, which is mainly cubic and monoclinic phases obtained by adding 2 parts of alumina to 100 parts of a mixture of 95 mol% of $ZrO_2$ and 5 mol% of $Y_2O_3$, and a spinal type porous layer 24 was interposed between the electrode 22 and an oxygen concentration cell 25 composed of zirconia ceramics in contact with each other. This assembly was inserted into a combustion exhaust gas and then an alternating current of 10 KHz and 50 mA was applied from an alternating current supply source 6 across the electrodes 22, 23 and further a part of the alternating current was rectified into a direct current component through a diode 12 and a resistor 13, which was applied simultaneously with the alternating current across the electrode 22 as an anode and the electrode 23 as a cathode. As a result, the temperature of the zirconia ceramics 21 constituting the oxygen concentration regulator was 600° C., the temperature of the oxygen concentration cell 25 was 400° C., and an atmosphere of approximately 100% oxygen was maintained in the porous layer 24.

The terminal voltage of the oxygen concentration cell 25 was measured by means of a voltage indicator by using this 100% oxygen as a standard gas, whereby an oxygen partial pressure of the combustion exhaust gas was determined.

Moreover, the frequencies at the points B and C of FIG. 3 in the zirconia ceramics 21 were 1 Hz and 1 KHz at 200° C., and 1 KHz and 1 MHz at 600° C., respectivley.

EXAMPLE 3

In another oxygen concentration regulator as shown in FIG. 12, 27 is a refractory material. In this embodiment, the refractory material is covered on at least one of electrodes 2, 3, thereby the electrode is hardly peeling off from solid electrolyte body by exposing various gases.

EXAMPLE 4

In another oxygen concentration regulator as shown in FIG. 13, 27 shows a refractory material and 28 shows an embedded electrode. In this embodiment, the embedded electrode 28 is not exposed to various gases, thereby the correct regulation can be expected by the use of an electrode 2 covered by refractory material 27 and the embedded electrode 28 without the deterioration of electrode.

EXAMPLE 5

In another oxygen concentration regulator as shown in FIG. 14, 2 shows an outer electrode, 3 shows an inner electrode and 10 shows another electrode. In this embodiment, DC supply source 4 is connected between electrodes 2 and 3 and AC supply source 6 is connected between electrodes 3 and 10, thereby the direct current for regulating oxygen concentration is affirmatively and correctly applied without influence of AC current.

As previously mentioned, in the oxygen concentration regulator according to the present invention, the solid electrolyte is directly self-heated, so that the power consumption becomes very small and the rapid heating is possible and the self-temperature control function of the solid electrolyte can be developed easily. Furthermore, the alternating voltage applied across the electrodes generates an alternating current component having a frequency at which a polarization of the alternating current component occurs mainly due to a polarization of the solid electrolyte but not to a polarization of an interface between the electrode and the solid electrolyte, so that the electrodes and solid electrolyte are less in the deterioration and excellent in the durability. The oxygen concentration regulator according to the present invention can be used, for example, in the control of atmosphere in heat-treating furnaces for the manufacture of semiconductor devices or as standard gas source in various gas sensors or the like. Therefore, the present invention is very useful for industrial applications.

What is claimed is:

1. An oxygen concentration regulator for regulating the oxygen concentration in gases, comprising:
    an oxygen ion conductive solid electrolyte body;
    a plurality of separate electrodes contacting the solid electrolyte body, at least two of said plurality of separate electrodes having the solid electrolyte body therebetween, thereby forming an electrolysis cell;
    AC power supplying means connected to at least two of said plurality of separate electrodes having the solid electrolyte body therebetween, for applying an AC voltage across said solid electrolyte body through said electrodes, said AC power supplying means being arranged to supply an AC voltage at a frequency sufficiently high such that an impedance between electrodes to which AC voltage is applied is largely independent of interface capacitances between said electrodes to which AC voltage is applied and a surface where said separate electrodes contact said electrolysis cell; and
    means for simultaneously applying a DC current across said at least two electrodes, said DC current regulating the oxygen concentration in gases.

2. The oxygen concentration regulator of claim 1, wherein at least one electrode of said at least two electrodes is embedded in said electrolyte body.

3. The oxygen concentration regulator of claim 1 or 2, further comprising a refractory material which covers at least one electrode of said at least two electrodes.

4. The oxygen concentration regulator of claim 1, further comprising means for limiting DC current level through the cell, and means for preventing DC current from flowing into the AC power supplying means.

5. The oxygen concentration regulator of claim 1, further comprising means for separating a circuit connected to AC power supplying means from a terminal of said electrolysis cell.

6. The oxygen concentration regulator of claim 1, wherein said AC power supplying means comprises an AC power source and at least one other electrode separate from said at least two electrodes forming said electrolysis cell.

7. The oxygen concentration regulator of claim 1, wherein at least a part of said means for flowing a DC current is a rectifying means for rectifying a part of said AC current into a DC current component.

8. An oxygen concentration regulator for regulating the oxygen concentration in gases, comprising:
    an oxygen ion conductive solid electrolyte body;
    a first set of at least two separate electrodes contacting the solid electrolyte body and having the solid electrolyte body therebetween, so as to form an electrolysis cell;

at least a third electrode separate from the electrodes of said first set; and

AC power supplying means connected to said at least a third electrode and at least one of said at least two separate electrodes, said at least a third electrode and said at least one of said at least two separate electrodes having the solid electrolyte body therebetween, for applying an AC electric voltage through said solid electrolyte body, said AC power supplying means being arranged to supply an AC voltage at a frequency sufficiently high that an impedance between said electrodes to which AC voltage is applied is largely independent of interface capacitances between said electrodes to which AC voltage is applied and a surface where said electrodes contact said solid electrolyte body; and means for flowing a DC current across said first set of electrodes, said DC current regulating the oxygen concentration in gases.

9. The oxygen concentration regulator of claim 8, wherein the solid electrolyte body has a tubular shape having an inside and an outside, the tube being closed at one end and one of said at least two separate electrodes is on the inside of the tube and adjacent the closed end, and another of said at least two separate electrodes is on the outside of the tube and adjacent the closed end.

10. The oxygen concentration regulator of claim 8, further comprising means for limiting DC current level through the cell, and means for preventing DC current from flowing into the AC power supplying means.

11. The oxygen concentration regulator of claim 8 or 9, wherein at least one of said electrodes is embedded in said electrolyte body.

12. The oxygen concentration regulator of claim 8 or 9, further comprising a refractory material which covers at least one of said electrodes.

13. The oxygen concentration regulator of claim 1 or 8, wherein an alternating current and an alternating voltage between the electrodes have a negative relation, in which when one increases, the other decreases.

14. An oxygen concentration regulating cell comprising:

an oxygen ion conductive solid electrolyte body of a tubular shape having an inner surface and an outer surface and a closed end, one of two separate cell electrodes contacting the inner surface of the tube and closed end, and a second of said two separate cell electrodes contacting the outer surface of said tube and closed end;

a third electrode separate from each of said two cell electrodes, said third electrode also contacting the outer surface of said tube;

AC power supplying means connected to said third electrode and said electrode contacting the inner surface of the tube for applying an AC electric voltage through said solid electrolyte body, said AC power supplying means being arranged to supply an AC voltage at a frequency sufficiently high such that an impedance between said electrodes to which AC voltage is applied is largely independent of interface capacitances between said electrodes to which AC voltage is applied and a surface where said electrodes contact said solid electrolyte body; and means for flowing a DC current across said two separate cell electrodes, said DC current regulating the oxygen concentration in gases.

15. A method of regulating oxygen concentration in a gaseous environment using an electrolysis cell comprising the steps of:

providing at least one electrolysis cell having at least two separate electrodes contacting an oxygen ion conductive solid electrolyte body and having the solid electrolyte body therebetween, at least one of said electrodes being exposed to gas in a gaseous environment;

heating the solid electrolyte body by applying an AC voltage across at least two separate electrodes having the solid electrolyte body therebetween, and thereby decreasing the impedance of said cell, and flowing the DC current across the electrodes which comprises the electrolysis cell when said solid electrolyte body is in its heated condition, said DC current regulating the oxygen concentration around at least one of said electrodes.

16. The method of claim 15, wherein at least a part of said DC current is supplied by rectifying a part of AC component.

17. A method of regulating oxygen concentration in a gaseous environment using an electrolysis cell comprising the steps of:

providing at least one electrolysis cell having at least two separate electrodes contacting an oxygen ion conductive solid electrolyte body, and having the solid electrolyte body therebetween, at least one of said at least two electrodes being exposed to gas in a gaseous environment;

applying an AC voltage to at least two separate electrodes contacting the oxygen ion conductive solid electrolyte and having the solid electrolyte body therebetween, with a frequency such that the cell is operated only at an AC frequency sufficiently high such that an impedance between said electrodes to which AC voltage is applied is largely independent of interface capacitances between said electrodes to which AC voltage is applied and a surface where said electrodes contact said electrolysis cell; and simultaneously applying a DC current across said electrodes, said DC current regulating the oxygen concentration in gases.

18. The method of claim 15 or 17, wherein the solid electrolyte body is heated to at least about 350° C. by application of the AC voltage across said electrodes.

19. The method of claim 15 or 17, wherein the solid electrolyte body has a tubular shape closed at one end and one of the two separate electrodes is on the inside of the tube and closed end, and the other of the two separate electrodes is on the outside of the tube and closed end.

* * * * *